(12) United States Patent
Jeppesen et al.

(10) Patent No.: US 6,300,339 B1
(45) Date of Patent: Oct. 9, 2001

(54) COMPOUNDS, THEIR PREPARATION AND USE

(75) Inventors: Lone Jeppesen, Virum; Paul Stanley Bury, Kobenhavn NV; Per Sauerberg, Farum, all of (DK)

(73) Assignees: Novo Nordisk A/S, Bagsvaerd (DK); Dr. Reddy's Research Foundation, Hyderabad (IN)

( * ) Notice: Subject to any disclaimer, the term of this patent is extended or adjusted under 35 U.S.C. 154(b) by 0 days.

(21) Appl. No.: 09/420,379

(22) Filed: Oct. 19, 1999

Related U.S. Application Data
(60) Provisional application No. 60/106,659, filed on Nov. 2, 1998.

(30) Foreign Application Priority Data

Oct. 21, 1998 (DK) .................................................. 01355/98

(51) Int. Cl.[7] ...................... A61K 31/4375; C07D 471/04
(52) U.S. Cl. .......................... 514/293; 514/290; 514/443; 514/468; 546/79; 546/81; 546/84; 546/101; 549/26; 549/43; 549/48; 549/387; 549/458
(58) Field of Search .................................. 516/84, 79, 81, 516/101; 549/43, 458, 26, 48, 387; 514/293, 443, 468, 290

(56) References Cited

FOREIGN PATENT DOCUMENTS

| WO 96/04260 | 2/1996 | (WO). |
| WO 96/04261 | 2/1996 | (WO). |
| WO 97/25042 | 7/1997 | (WO). |
| WO 97/36579 | 10/1997 | (WO). |
| WO 99/19313 | 4/1999 | (WO). |

OTHER PUBLICATIONS

Jeppeson et al., Chemical Abstracts, vol. 132:308360, 2000.*
Abstract of Japanese Patent No. JP 10182550.

* cited by examiner

*Primary Examiner*—Richard L. Raymond
(74) *Attorney, Agent, or Firm*—Reza Green, Esq.; Valeta A. Gregg, Esq.

(57) ABSTRACT

The present invention relates to compounds of formula (I)

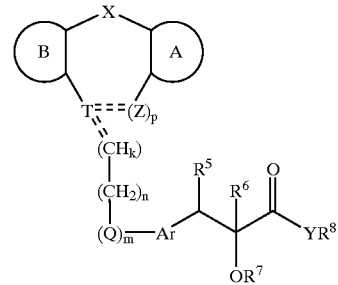

(Ia)

wherein A, B, Q, T, X, Y, Z, $R^5$, $R^6$, $R^7$, $R^8$, Ar, k, m, n and p are as defined in the specification. These compounds are useful in treating or preventing conditions mediated by nuclear receptors, in particular the Peroxisome Proliferator-Activated Receptors (PPAR).

52 Claims, No Drawings

COMPOUNDS, THEIR PREPARATION AND USE

CROSS-REFERENCE TO RELATED APPLICATIONS

This application claims priority under 35 U.S.C. 119 of U.S. provisional application no. 60/106,659 filed Nov. 2, 1998 and Danish application no. PA 1998 01355 filed Oct. 21, 1998, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilized in the treatment of conditions mediated by nuclear receptors, in particular the Peroxisome Proliferator-Activated Receptors (PPAR). The present compounds reduce blood glucose and triglyceride levels and are accordingly useful for the treatment of ailments and disorders such as diabetes and obesity.

The present invention also relates to a process for the preparation of the above said novel compounds, their derivatives, their analogs, their tautomeric forms, their stereoisomers, their polymorphs, their pharmaceutically acceptable salts, pharmaceutically acceptable solvates and pharmaceutical compositions containing them.

The compounds are useful for the treatment and/or prophylaxis of insulin resistance (type 2 diabetes), impaired glucose tolerance, dyslipidemia, disorders related to Syndrome X such as hypertension, obesity, insulin resistance, hyperglycemia, atherosclerosis, hyperlipidemia, coronary artery disease and other cardiovascular disorders. The compounds of the present invention are also useful for the treatment of certain renal diseases including glomerulonephritis, glomerulosclerosis, nephrotic syndrome, hypertensive nephrosclerosis. These compounds may also be useful for improving cognitive functions in dementia, treating diabetic complications, psoriasis, polycystic ovarian syndrome (PCOS) and prevention and treatment of bone loss, e.g. osteoporosis.

BACKGROUND OF THE INVENTION

Coronary artery disease (CAD) is the major cause of death in type 2 diabetic and metabolic syndrome patients (i.e. patients that fall within the 'deadly quartet' category of impaired glucose tolerance, insulin resistance, hypertriglyceridemia and/or obesity).

The hypolipidemic fibrates and antidiabetic thiazolidinediones separately display moderately effective triglyceride-lowering activities although they are neither potent nor efficacious enough to be a single therapy of choice for the dyslipidemia often observed in type 2 diabetic or metabolic syndrome patients. The thiazolidinediones also potently lower circulating glucose levels of type 2 diabetic animal models and humans. However, the fibrate class of compounds are without beneficial effects on glycemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue. Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence. PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarized as follows: (I) an increased lipolysis and clearance of remnant particles, due to changes in lipoprotein lipase and apo C-II levels, (II) a stimulation of cellular fatty acid uptake and their subsequent conversion to acyl-CoA derivatives by the induction of fatty acid binding protein and acyl-CoA synthase, (III) an induction of fatty acid b-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726,PCT Publications nos. WO91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

It seems more and more apparent that glucose lowering as a single approach does not overcome the macrovascular complications associated with type 2 diabetes and metabolic syndrome. Novel treatments of type 2 diabetes and metabolic syndrome must therefore aim at lowering both the overt hypertriglyceridemia associated with these syndromes as well as alleviation of hyperglycemia.

The clinical activity of fibrates and thiazolidinediones indicates that research for compounds displaying combined PPARα and PPARγ activation should lead to the discovery of efficacious glucose and triglyceride lowering drugs that have great potential in the treatment of type 2 diabetes and the metabolic syndrome (i.e. impaired glucose tolerance, insulin resistance, hypertriglyceridemia and/or obesity).

DETAILED DESCRIPTION OF THE INVENTION

Accordingly, the present invention relates to compounds of formula (Ia):

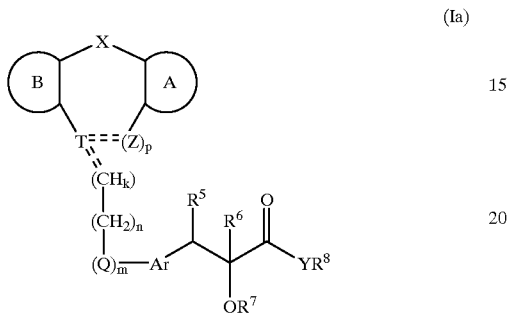

wherein ring A represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{,1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano; ring B represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(CHR$^9$)—CH=CH—, —(CHR$^9$)—CH$_2$—CH$_2$—, —(C=O)—, —O—CH$_2$—O—, —(NR$^9$)—, —(NR$^9$)—S(O$_2$)—, —CH=(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$, wherein R$^9$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, $C_{1-6}$alkoxy, amino; optionally substituted with one or more $C_{1-6}$alkyl, perhalomethyl or aryl;

T is >N—, >CH—, >C<, —CH$_2$—N<;

Z is —CH$_2$—, =CH—, >N—, —O—, —S—, >CO, >SO, >SO$_2$, >NR$^{13}$, wherein R$^{13}$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$, $_2$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{14}$, or —SO$_2$R$^{15}$, wherein R$^{14}$ and R$^{15}$ independently of each other are selected from hydroxy, halogen, $C_{1-6}$alkoxy, amino optionally substituted with one or more $C_{1-6}$alkyl, perhalomethyl or aryl;

Q is —O—, —S—, >SO$_2$, >NR$^{16}$, wherein R$^{16}$ is hydrogen or $C_{1-6}$alkyl;

k is 1 or 2;

T═══(Z)$_p$ and T═══(CH$_k$) independently of each other represents a single bond or a double bond, provided that both are not a double bond at the same time;

Ar represents arylene, heteroarylene, or a divalent heterocyclic group optionally substituted with one or more $C_{1-6}$alkyl or aryl;

R$^5$ represents hydrogen, hydroxy, halogen, $C_{1-12}$alkoxy, $C_{12}$alkyl, $C_{4-12}$-alkenynyl, $C_{2-12}$-alkenyl, $C_{2-12}$-alkynyl or aralkyl; optionally substituted with one or more halogen, perhalomethyl, hydroxy, nitro or cyano; or R$^5$ forms a bond together with R$^6$;

R$^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl, acyl or aralkyl; optionally substituted with one or more halogen, perhalomethyl, hydroxy, nitro or cyano; or R$^6$ forms a bond together with R$^5$;

R$^7$ represents hydrogen, $C_{1-12}$alkyl, $C_{4-12}$-alkenynyl, $C_{2-12}$-alkenyl, $C_{2-12}$-alkynyl, aryl, aralkyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, acyl, heterocyclyl, heteroaryl or heteroaralkyl groups; optionally substituted with one or more halogen, perhalomethyl, hydroxy, nitro or cyano;

R$^8$ represents hydrogen, $C_{1-12}$alkyl, $C_{4-12}$-alkenynyl, $C_{2-12}$-alkenyl, $C_{2-12}$-alkynyl, aryl, aralkyl, heterocyclyl, heteroaryl or heteroaralkyl groups; optionally substituted with one or more halogen, perhalomethyl, hydroxy, nitro or cyano;

Y represents oxygen, sulphur or $NR^{10}$, where $R^{10}$, represents hydrogen, $C_{1-12}$alkyl, aryl, hydroxy$C_{1-12}$alkyl or aralkyl groups or when Y is $NR^{10}$, $R^8$ and $R^{10}$ may form a 5 or 6 membered nitrogen containing ring, optionally substituted with one or more $C_{1-6}$, alkyl;

p is an integer ranging from 0 to 1, n is an integer ranging from 0 to 3 and m is an integer ranging from 0 to 1;

provided that A or B does not represent phenyl;

or a pharmaceutically acceptable salt thereof.

In a preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, $-COR^{11}$, or $-SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano;

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, acylamino, $C_{1-7}$, alkylamino, arylamino, aralkylamino, $C_{1-7}$alkoxy$C_{1-7}$alkyl, aryloxy$C_{1-7}$alkyl, aralkoxy$C_{1-7}$alkyl, or $C_{1-7}$alkylthio.

In another preferred embodiment, the present invention is concerned with compounds of formula I wherein ring A represents a 5–6 membered cyclic ring, optionally substituted with one or more halogen, $C_{1-7}$alkyl, $C_{1-7}$alkoxy, aryl, or aryloxy.

In another preferred embodiment, the present invention is concerned with compounds of formula I wherein ring A represents a 5–6 membered cyclic ring, optionally substituted with one or more $C_{1-7}$alkoxy.

In another preferred embodiment, the present invention is concerned with compounds of formula I wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$aralkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, $-COR^{11}$, or $-SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano.

In another preferred embodiment, the present invention is concerned with compounds of formula I wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$, alkylthio, thio$C_{1-7}$alkyl, $C_{1-7}$alkoxycarbonylamino, aryloxycarbonylamino, aralkoxycarbonylamino.

In another preferred embodiment, the present invention is concerned with compounds of formula I wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, acylamino, $C_{1-7}$alkylamino, arylamino, aralkylamino, $C_{1-7}$alkoxy$C_{1-7}$alkyl, aryloxy$C_{1-7}$alkyl, aralkoxy$C_{1-7}$alkyl, or $C_{1-7}$alkylthio.

In another preferred embodiment, the present invention is concerned with compounds of formula I wherein ring B represents a 5–6 membered cyclic ring, optionally substituted with one or more halogen, $C_{1-7}$alkyl, $C_{1-7}$alkoxy, aryl, or aryloxy.

In another preferred embodiment, the present invention is concerned with compounds of formula I wherein ring B represents a 5–6 membered cyclic ring, optionally substituted with one or more $C_{1-7}$alkoxy.

In another preferred embodiment, the present invention is concerned with compounds of formula I wherein X is a valence bond, $-(CHR^9)-$, $-(CHR^9)-CH_2-$, $-CH=CH-$, $-O-$, $-O-(CHR^9)-$, $-S-(CHR^9)-$, $-(NR^9)-CH_2-$, $-(CHR^9)-CH=CH-$, $-(CHR^9)-CH_2-CH_2-$, $-(C=O)-$, $-O-CH_2-O-$, $-(NR^9)-$, $-(NR^9)-S(O_2)-$, $-CH=(CR^9)-$, $-(CO)-(CHR^9)-$, $-CH_2-(SO)-$, $-S-$, $-(SO)-$, $-(SO_2)-$, $-CH_2-(SO_2)-$, $-CH_2-O-CH_2-$, wherein $R^9$ is hydrogen, halogen, hydroxy, cyano, $C_{1-7}$alkyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-7}$alkyl-amino, arylamino, aralkylamino, amino $C_{1-7}$alkyl, $C_{1-7}$alkoxycarbonyl, aryloxycarbonyl, aralkoxycarbonyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, $-COR^{11}$, or $-SO_2R^{12}$, wherein $R^{11}$ and $R^{12}$ independently of each other are selected from hydroxy, halogen, $C_{1-6}$alkoxy, amino optionally substituted with one or more $C_{1-6}$alkyl, perhalomethyl or aryl.

In another preferred embodiment, the present invention is concerned with compounds of formula I wherein X is a valence bond, $-(CHR^9)-$, $-(CHR^9)-CH_2-$, $-CH=CH-$, $-O-$, $-O-(CHR^9)-$, $-S-(CHR^9)-$, $-(NR^9)-CH_2-$, $-(CHR^9)-CH=CH-$, $-(CHR^9)-CH_2-CH_2-$, $-(C=O)-$, $-O-CH_2-O-$, $-(NR^9)-$, $-(NR^9)-S(O_2)-$, $-CH=(CR^9)-$, $-(CO)-(CHR^9)-$, $-CH_2-(SO)-$, $-S-$, $-(SO)-$, —(SO$_2$)—, —CH$_2$—(SO$_2$)—, —CH$_2$—O—CH$_2$—, wherein R$^9$ is hydrogen, halogen, hydroxy, C$_{1-7}$alkyl, C$_{1-7}$alkoxy, or aryl.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(C=O)—, —O—CH$_2$—, —(NR$^9$)—, —CH=(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$—, wherein R$^9$ is hydrogen, halogen, hydroxy, C$_{1-7}$alkyl, C$_{1-7}$alkoxy, or aryl.

In another preferred embodiment, the present invention is concerned with compounds of formula I wherein T is >N—, >CH— or >C<.

In another preferred embodiment, the present invention is concerned with compounds of formula I wherein Z is —CH$_2$—, =CH—, >N—, —O—, —S—, >CO, >SO, >SO$_2$, >NR$^{13}$, wherein R$^{13}$ is hydrogen, C$_{1-7}$alkyl, aryl, aralkyl, heterocyclyl, heteroaryl, heteroaralkyl, acyl, acyloxy, hydroxyalkyl, aminoC$_{1-7}$alkyl, C$_{1-7}$alkoxycarbonyl, aryloxycarbonyl, aralkoxycarbonyl, C$_{1-7}$alkoxyC$_{1-7}$alkyl, aryloxyC$_{1-7}$alkyl, aralkoxy C$_{1-7}$alkyl, thioC$_{1-7}$alkyl, —COR$^{14}$, or —SO$_2$R$^{15}$, wherein R$^{14}$ and R$^{15}$ independently of each other are selected from hydroxy, C$_{1-6}$alkoxy, amino optionally substituted with one or more C$_{1-6}$alkyl, perhalomethyl or aryl.

In another preferred embodiment, the present invention is concerned with compounds of formula I wherein Z is —CH$_2$—, =CH—, >N—, —O—, —S—, >CO, >SO, >SO$_2$, >NR$^{13}$, wherein R$^{13}$ is hydrogen, C$_{1-7}$alkyl, aryl, aralkyl, heterocyclyl, heteroaryl, heteroaralkyl, acyl, acyloxy, hydroxyalkyl, C$_{1-7}$alkoxyC$_{1-7}$alkyl, aryloxyC$_{1-7}$alkyl, aralkoxyC$_{1-7}$alkyl.

In another preferred embodiment, the present invention is concerned with compounds of formula I wherein Z is —CH$_2$—, =CH—, >N—, —O—, —S—, >CO, >SO, >SO$_2$, >NR$^{13}$, wherein R$^{13}$ is hydrogen, C$_{1-7}$alkyl.

In another preferred embodiment, the present invention is concerned with compounds of formula I wherein Q is —O—, —S—, >SO$_2$, >NR$^{16}$, wherein R$^{16}$ is hydrogen or methyl.

In another preferred embodiment, the present invention is concerned with compounds of formula I wherein Ar represents arylene optionally substituted with one or more C$_{1-6}$, alkyl or aryl.

In another preferred embodiment, the present invention is concerned with compounds of formula I wherein Ar represents phenyl.

In another preferred embodiment, the present invention is concerned with compounds of formula I wherein R$^5$ represents hydrogen, hydroxy, halogen, C$_{1-7}$alkoxy, C$_{1-7}$alkyl, C$_{4-7}$-alkenynyl, C$_{2-7}$-alkenyl, C$_{2-7}$-alkynyl or aralkyl; or R$^5$ forms a bond together with R$_6$.

In another preferred embodiment, the present invention is concerned with compounds of formula I wherein R$_6$ represents hydrogen, or R$^5$ forms a bond together with R$^6$.

In another preferred embodiment, the present invention is concerned with compounds of formula I wherein R$^6$ represents hydrogen, C$_{1-7}$alkoxy, C$_{1-7}$alkyl, C$_{4-7}$-alkenynyl, C$_{2-7}$-alkenyl, C$_{2-7}$-alkynyl, acyl or aralkyl or R$^6$ forms a bond together with R$^5$.

In another preferred embodiment, the present invention is concerned with compounds of formula I wherein R$^6$ represents hydrogen or R$^6$ forms a bond together with R$^5$.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl, C$_{2-7}$-alkynyl, aryl, aralkyl, C$_{1-7}$alkoxyC$_{1-7}$alkyl, C$_{1-7}$alkoxycarbonyl, aryloxycarbonyl, C$_{1-7}$alkylaminocarbonyl, arylaminocarbonyl, acyl, heterocyclyl, heteroaryl or heteroaralkyl groups.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl, C$_{2-7}$-alkynyl.

In another preferred embodiment, the present invention is concerned with compounds of formula I wherein R$^7$ represents C$_{1-2}$alkyl.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl, aralkyl, heterocyclyl, heteroaryl or heteroaralkyl groups; optionally substituted with one or more halogen, perhalomethyl, hydroxy, nitro or cyano.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl or aralkyl.

In another preferred embodiment, the present invention is concerned with compounds of formula I wherein R$^8$ represents hydrogen or C$_{2-7}$alkyl.

In another preferred embodiment, the present invention is concerned with compounds of formula I wherein Y represents oxygen, sulphur or NR$^{10}$, where R$^{10}$ represents hydrogen, C$_{1-7}$alkyl, aryl, hydroxyC$_{1-7}$alkyl or aralkyl groups.

In another preferred embodiment, the present invention is concerned with compounds of formula I wherein Y represents oxygen.

In another preferred embodiment, the present invention is concerned with compounds of formula I wherein A is 5-membered cyclic ring containing S.

In another preferred embodiment, the present invention is concerned with compounds of formula I wherein B is 5-membered cyclic ring containing S.

In another preferred embodiment, the present invention is concerned with compounds of formula I wherein X is —(CHR$^9$)—CH$_2$—, wherein R$^9$ is H.

In another preferred embodiment, the present invention is concerned with compounds of formula I wherein T is >C<.

In another preferred embodiment, the present invention is concerned with compounds of formula I wherein p is 0.

In another preferred embodiment, the present invention is concerned with compounds of formula I wherein k is 1.

In another preferred embodiment, the present invention is concerned with compounds of formula I wherein n is 1.

In another preferred embodiment, the present invention is concerned with compounds of formula I wherein m is 1.

In another preferred embodiment, the present invention is concerned with compounds of formula I wherein Q is —O—.

In another preferred embodiment, the present invention is concerned with compounds of formula I wherein Ar is phenylene.

In another preferred embodiment, the present invention is concerned with compounds of formula I wherein R$^5$ is H.

In another preferred embodiment, the present invention is concerned with compounds of formula I wherein R$^6$ is H.

In another preferred embodiment, the present invention is concerned with compounds of formula I wherein R$^7$ is ethyl.

In another preferred embodiment, the present invention is concerned with compounds of formula I wherein R$^8$ is H.

Preferred compounds of the invention are:

3-{4-[2-(4,5-dihydro-cyclohepta[2,1-b 4,5-b']dithiophen-9-ylidene)-ethoxy]-phenyl}-2-ethoxypropionic acid,
Ethyl 3-{4-[2-(9H-1,8-diazafluoren-9-yl)-ethoxy]-phenyl})-2-ethoxypropionate,
3-{4-[2-(9H-1,8-Diazafluoren9-yl)ethoxy]-phenyl}-2-ethoxypropionic acid,
Ethyl 3-{4-[3-(9H-1,8-Diazafluoren-9-yl)-propoxy]-phenyl}-2-ethoxypropionate,
3-{4-[3-(9H-1,8-Diazafluoren-9-yl)-propoxy]-phenyl}-2-ethoxypropionic acid,
Ethyl 3-{4-[2-(9H-1,8-Diazafluoren-9-yl)-ethoxy]-phenyl}-2-methoxypropionate,
3-{4-[2-(9H-1,8-Diazafluoren-9-yl)-ethoxy]-phenyl}-2-methoxypropionic acid,
Ethyl 3-{4-[3-(9H-1,8-Diazafluoren-9-yl)-propoxy]-phenyl}-2-methoxypropionate,
3-{4-[3-(9H-1,8-Diazafluoren-9-yl)-propoxy]-phenyl}-2-methoxypropionic acid,
Ethyl 3-{4-[2-(1,8-diazafluoren-9-ylidene)-ethoxy]-phenyl}-2-ethoxypropionate,
3-{4-[2-(1,8-Diazafluoren-9-ylidene)-ethoxy]-phenyl}-2-ethoxypropionic acid,
Ethyl 3-{4-[3-(1,8-Diazafluoren-9-ylidene)-propoxy]-phenyl}-2-ethoxypropionate,
3-{4-[3-(1,8-Diazafluoren-9-ylidene)-propoxy]-phenyl}-2-ethoxypropionic acid,
Ethyl 3-{4-[2-(1,8-Diazafluoren-9-ylidene)-ethoxy]-phenyl}-2-methoxypropionate,
3-{4-[2-(1,8-Diazafluoren-9-ylidene)-ethoxy]-phenyl}2-methoxypropionic acid,
Ethyl 3-{4-[3-(1,8-Diazafluoren-9-ylidene)-propoxy]-phenyl}-2-methoxypropionate,
3-{4-[3-(1,8-Diazafluoren-9-ylidene)-propoxy]-phenyl}-2-methoxypropionic acid,
Ethyl 3-{4-[2-(9H-1,7-diazafluoren-9-yl)-ethoxy]-phenyl}-2-ethoxypropionate,
3-{4-[2-(9H-1,7-Diazafluoren-9-yl)-ethoxy]-phenyl}-2-ethoxypropionic acid,
Ethyl 3-{4-[3-(9H-1,7-Diazafluoren-9-yl)-propoxy]-phenyl}-2-ethoxypropionate,
3-{4-[3-(9H-1,7-Diazafluoren-9-yl)-propoxy]-phenyl}-2-ethoxypropionic acid,
Ethyl 3-{4-[2-(9H-1,7-Diazafluoren-9-yl)-ethoxy]-phenyl}-2-methoxypropionate,
3-{4-[2-(9H-1,7-Diazafluoren-9-yl)-ethoxy]-phenyl}-2-methoxypropionic acid,
Ethyl 3-{4-[3-(9H-1,7-Diazafluoren-9-yl)-propoxy]-phenyl}-2-methoxypropionate,
3-{4-[3-(9H-1,7-Diazafluoren-9-yl)-propoxy]-phenyl}-2-methoxypropionic acid,
Ethyl 3-{4-[2-(1,7-diazafluoren-9-ylidene)-ethoxy]-phenyl}-2-ethoxypropionate,
3-{4-[2-(1,7-Diazafluoren-9-ylidene)-ethoxy]-phenyl}-2-ethoxypropionic acid,
Ethyl 3-{4-[3-(1,7-Diazafluoren-9-ylidene)propoxy] phenyl}-2-ethoxypropionate,
3-{4-[3-(1,7-Diazafluoren-9-ylidene)-propoxy]-phenyl}-2-ethoxypropionic acid,
Ethyl 3-{4-[2-(1,7-Diazafluoren-9-ylidene)-ethoxy]-phenyl}-2-methoxypropionate,
3-{4-[2-(1,7-Diazafluoren-9-ylidene)-ethoxy]-phenyl}-2-methoxypropionic acid,
Ethyl 3-{4-[3-(1,7-Diazafluoren-9-ylidene)-propoxy]-phenyl}-2-methoxypropionate,
3-{4-[3-(1,7-Diazafluoren-9-ylidene)-propoxy]-phenyl}-2-methoxypropionic acid,
Ethyl 3-{4-[2-(9H-2,7-diazafluoren-9-yl)-ethoxy]-phenyl}-2-ethoxypropionate,
3-{4-[2-(9H-2,7-Diazafluoren-9-yl)-ethoxy]-phenyl}-2-ethoxypropionic acid,
Ethyl 3-{4-[3-(9H-2,7-Diazafluoren-9-yl)-propoxy]-phenyl}-2-ethoxypropionate,
3-{4-[3-(9H-2,7-Diazafluoren-9-yl)-propoxy]-phenyl}-2-ethoxypropionic acid,
Ethyl 3-{4-[2-(9H-2,7-Diazafluoren-9-yl)-ethoxy]-phenyl}-2-methoxypropionate,
3-{4-[2-(9H-2,7-Diazafluoren-9-yl)-ethoxy]-phenyl}-2-methoxypropionic acid,
Ethyl 3-{4-[3-(9H-2,7-Diazafluoren-9-yl)-propoxy]-phenyl}-2-methoxypropionate,
3-{4-[3-(9H-2,7-Diazafluoren-9-yl)-propoxy]-phenyl}-2-methoxypropionic acid,
Ethyl 3-{4-[2-(2,7-diazafluoren-9-ylidene)-ethoxy]-phenyl}-2-ethoxypropionate,
3-{4-[2-(2,7-Diazafluoren-9-ylidene)-ethoxy]-phenyl}-2-ethoxypropionic acid,
Ethyl 3-{4-[3-(2,7-Diazafluoren-9-ylidene)-propoxy]-phenyl}-2-ethoxypropionate,
3-{4-[3-(2,7-Diazafluoren-9-ylidene)-propoxy]-phenyl}-2-ethoxypropionic acid,
Ethyl 3-{4-[2-(2,7-Diazafluoren-9-ylidene)-ethoxy]-phenyl}-2-methoxypropionate,
3-{4-[2-(2,7-Diazafluoren-9-ylidene)-ethoxy]-phenyl}-2-methoxypropionic acid,
Ethyl 3-{4-[3-(2,7-Diazafluoren-9-ylidene)-propoxy]-phenyl}-2-methoxypropionate,
3-{4-[3-(2,7-Diazafluoren-9-ylidene)-propoxy]-phenyl}-2-methoxypropionic acid,
Ethyl 3-{4-[2-(9H-3,6-diazafluoren-9yl)-ethoxy]-phenyl}-2-ethoxypropionate,
3-{4-[2-(9H-3,6-Diazafluoren-9-yl)-ethoxy]-phenyl}-2-ethoxypropionic acid,
Ethyl 3-{4-[3-(9H-3,6-diazafluoren-9-yl)-propoxy]-phenyl}-2-ethoxypropionate,
3-{4-[3-(9H-3,6-Diazafluoren-9-yl)-propoxy]-phenyl}-2-ethoxypropionic acid,
Ethyl 3-{4-[2-(9H-3,6-diazafluoren-9-yl)-ethoxy] phenyl}-2-methoxypropionate,
3-{4-[2-(9H-3,6-Diazafluoren-9-yl)-ethoxy]-phenyl}-2-methoxypropionic acid,
Ethyl 3-{4-[3-(9H-3,6-diazafluoren-9-yl)-propoxy]-phenyl}-2-methoxypropionate,
3-{4-[3-($^9$H-3,6-Diazafluoren-9-yl)-propoxy]-phenyl}-2-methoxypropionic acid,
Ethyl 3-{4-[2-(3,6-diazafluoren-9-ylidene)-ethoxy] phenyl}-2-ethoxypropionate,
3-{4-[2-(3,6-Diazafluoren-9-ylidene)-ethoxy]-phenyl}-2-ethoxypropionic acid,
Ethyl 3-{4-[3-(3,6-diazafluoren-9-ylidene)-propoxy]-phenyl}-2-ethoxypropionate,
3-{4-[3-(3,6-Diazafluoren-9-ylidene)-propoxy]-phenyl}-2-ethoxypropionic acid,
Ethyl 3-{4-[2-(3,6-diazafluoren-9-ylidene)-ethoxy]-phenyl}-2-methoxypropionate, 3-{4-[2-(3,6-Diazafluoren-9-ylidene)-ethoxy]-phenyl}-2-methoxypropionic acid, Ethyl 3-{4-[3-(3,6-Diazafluoren-9-ylidene)-propoxy]-phenyl}-2-methoxypropionate, 3-{4-[3-(3,6-Diazafluoren-9-ylidene)-propoxy]-phenyl}-2-methoxypropionic acid, Ethyl 3-{4-[2-(cyclopenta[1,2-b;4,3-b']difuran-7-ylidene)-ethoxy]phenyl}-2-ethoxypropionate, 3-{4-[2-(Cyclopenta[1,2-b;4,3-b']difuran-7-ylidene)-ethoxy]-phenyl}-2-ethoxypropionic acid, Ethyl 3-{4-[3-(cyclopenta[1,2-b;4,3-b']difuran-7-ylidene)-propoxy]-phenyl}-2-ethoxypropionate, 3-{4-[3-(Cyclopenta[1,2-b;4,3-b']difuran-7-ylidene)-propoxy]-phenyl}-2-ethoxypropionic acid, Ethyl 3-{4-[2-(cyclopenta[1,2-b;4,3-b']difuran-7-ylidene)-ethoxy]-phenyl}-2-methoxypropionate, 3-{4-[2-(Cyclopenta[1,2-b;4,3-b']difuran-7-ylidene)-ethoxy]-phenyl}-2-methoxypropionic acid, Ethyl 3-{4-[3-(cyclopenta[1,2-b;4,3-b']difuran-7-ylidene)-propoxy]-phenyl}-2-methoxypropionate, 3-{4-[3-(Cyclopenta[1,2-b;4,3-b']difuran-7-ylidene)-propoxy]-phenyl}-2-methoxy-propionic acid, Ethyl 3-{4-[2-(7H-cyclopenta[1,2-b;4,3-b']difuran-7-yl)-ethoxy]-phenyl}-2-ethoxypropionate, 3-{4-[2-(7H-Cyclopenta[1,2-b;4,3-b']difuran-7-yl)-ethoxy]-phenyl}-2-ethoxypropionic acid, Ethyl 3-{4-[3-(7H-cyclopenta[1,2-b;4,3-b']difuran-7-yl)-propoxy]-phenyl}-2-ethoxy-propionate, 3-{4-[3-(7H-Cyclopenta[1,2-b;4,3-b']difuran-7-yl)-propoxy]-phenyl}-2-ethoxypropionic acid, Ethyl 3-{4-[2-(7H-cyclopenta[1,2-b;4,3-b']difuran-7-yl)-ethoxy]-phenyl}-2-methoxy-propionate, 3-{4-[2-(7H-Cyclopenta[1,2-b;4,3-b']difuran-7-yl)-ethoxy]-phenyl}-2-methoxypropionic acid, Ethyl 3-{4-[3-(7H-cyclopenta[1,2-b;4,3-b']difuran-7-yl)-propoxy]-phenyl}-2-methoxypropionate, 3-{4-[3-(7H-Cyclopenta[1,2-b;4,3-b']difuran-7-yl)-propoxy]-phenyl}-2-methoxy-propionic acid, Ethyl 3-{4-[2-(cyclopenta[1,2-b;4,3-b']dithiophen-7-ylidene)-ethoxy]-phenyl}-2-ethoxypropionate, 3-{4-[2-(Cyclopenta[1,2-b;4,3-b']dithiophen-7-ylidene)-ethoxy]-phenyl}-2-ethoxypropionic acid, Ethyl 3-{4-[3-(cyclopenta[1,2-b;4,3-b']dithiophen-7-ylidene)-propoxy]-phenyl}-2-ethoxypropionate, 3-{4-[3-(Cyclopenta[1,2-b;4,3-b']dithiophen-7-ylidene)-propoxy]-phenyl}-2-ethoxypropionate acid, Ethyl 3-{4-[2-(cyclopenta[1,2-b;4,3-b']dithiophen-7-ylidene)-ethoxy]-phenyl}-2-methoxypropionate, 3-{4-[2-(Cyclopenta[1,2-b;4,3-b']dithiophen-7-ylidene)-ethoxy]-phenyl}-2-methoxypropionic acid, Ethyl 3-{4-[3-(cyclopenta[1,2-b;4,3-b']dithiophen-7-ylidene)-propoxy]-phenyl}-2-methoxypropionate, 3-{4-[3-(Cyclopenta[1,2-b;4,3-b']dithiophen-7-ylidene)-propoxy]-phenyl}-2-methoxy-propionic acid, Ethyl 3-{4-[2-(7H-cyclopenta[1,2-b;4,3-b']dithiophen-7-yl)-ethoxy]-phenyl}-2-ethoxypropionate, 3-{4-[2-(7H-Cyclopenta[1,2-b;4,3-b']dithiophen-7-yl)-ethoxy]-phenyl}-2-ethoxypropionic acid, Ethyl 3-{4-[3-(7H-cyclopenta[1,2-b;4,3-b']dithiophen-7-yl)-propoxy]-phenyl}-2-ethoxypropionate, 3-{4-[3-(7H-Cyclopenta[1,2-b;4,3-b']dithiophen-7-yl)-propoxy]-phenyl}-2-ethoxypropionic acid, Ethyl 3-{4-[2-(7H-cyclopenta[1,2-b;4,3-b']dithiophen-7-yl)-ethoxy]-phenyl}-2-methoxypropionate, 3-{4-[2-(7H-Cyclopenta[1,2-b;4,3-b']dithiophen-7-yl)-ethoxy]-phenyl}-2-methoxypropionic acid, Ethyl 3-{4-[3-(7H-cyclopenta[1,2-b;4,3-b']dithiophen-7-yl)-propoxy]-phenyl}-2-methoxypropionate, 3-{4-[3-(7H-Cyclopenta[1,2-b;4,3-b']dithiophen-7-yl)-propoxy]-phenyl}-2-methoxy-propionic acid;

or a pharmaceutically acceptable salt thereof.

A further preferred compound of the invention is:

3-{4-[2-(4,5-dihydro-cyclohepta[2,1-b4,5-b']dithiophen-9-ylidene)-ethoxy]-phenyl}-2-ethoxypropionic acid;

or a pharmaceutically acceptable salt thereof.

In the above structural formulas and throughout the present specification, the following terms have the indicated meaning:

The terms "$C_{1-12}$-alkyl" as used herein, alone or in combination is intended to include those alkyl groups of the designated length in either a linear or branched or cyclic configuration, represents e.g. cyclopropyl, cyclobutyl, cyclopentyl, cyclohexyl, cycloheptyl and cyclooctyl and the like. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like.

The terms "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl, and the like.

The terms "$C_{2-n'}$-alkynyl" wherein n' can be from 3 through 15, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten4-yne, 3-penten-1-yne, 1,3-hexadiene-5-yne and the like.

The term "$C_{1-12}$-alkoxy" as used herein, alone or in combination is intended to include those $C_{1-12}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "$C_{1-6}$alkoxycarbonyloxy" is intended to include the above defined $C_{1-6}$-alkoxy groups attached to a carbonyloxy moiety, eg. methoxycarbonyloxy, ethoxycarbonyloxy, etc.

As used herein the term "$C_{4-12}$-(cycloalkylalkyl)" represents a branched or straight alkyl group substituted at a carbon with a cycloalkyl group. Examples of such groups include, but are not limited to, cyclopropylethyl, cyclobutylmethyl, 2-(cyclohexyl)ethyl, cyclohexylmethyl, 3-(cyclopentyl)-1-propyl, and the like.

The term "$C_{1-12}$-alkylthio" as used herein, alone or in combination, refers to a straight or branched or cyclic monovalent substituent comprising a $C_{1-12}$-alkyl group linked through a divalent sulfur atom having its free valence bond from the sulfur atom and having 1 to 12 carbon atoms e.g. methylthio, ethylthio, propylthio, butylthio, pentylthio. Example of cyclic alkylthio are cyclopropylthio, cyclobutylthio, cyclopentylthio and cyclohexylthio.

The term "$C_{1-12}$alkylamino" as used herein, alone or in combination, refers to a straight or branched or cyclic monovalent substituent comprising a $C_{1-12}$-alkyl group linked through amino having a free valence bond from the nitrogen atom e.g. methylamino, ethylamino, propylamino, butylamino, pentylamino. Example of cyclic alkylamino are cyclopropylamino, cyclobutylamino, cyclopentylamino and cyclohexylamino.

The term "hydroxy$C_{1-12}$alkyl" as used herein, alone or in combination, refers to a $C_{1-12}$alkyl as defined herein whereto is attached a hydroxy group, e.g., hydroxyethyl, 1-hydroxypropyl, 2-hydroxypropyl etc.

The term "arylamino" as used herein, alone or in combination, refers to an aryl as defined herein linked through amino having a free valence bond from the nitrogen atom e.g. phenylamino, naphthylamino, etc.

The term "aralkylamino" as used herein, alone or in combination, refers to an aralkyl as defined herein linked through amino having a free valence bond from the nitrogen atom e.g. benzylamino, phenethylamino, 3-phenylpropylamino, 1-naphtylmethylamino, 2-(1-naphtyl)ethylamino and the like.

The term "amino$C_{1-12}$alkyl" as used herein, alone or in combination, refers to a $C_{1-12}$alkyl as defined herein whereto is attached an amino group, e.g. aminoethyl, 1-aminopropyl, 2-aminopropyl etc.

The term "aryloxycarbonyl" as used herein, alone or in combination, refers to an aryloxy as defined herein linked through a carbonyl having a free valence bond from the carbon atom, e.g. phenoxycarbonyl, 1-naphthyloxycarbonyl or 2-naphthyloxycarbonyl, etc.

The term "aralkoxycarbonyl" as used herein, alone or in combination, refers to an aralkoxy as defined herein linked through a carbonyl having a free valence bond from the carbon atom, e.g. benzyloxycarbonyl, phenethoxycarbonyl, 3-phenylpropoxycarbonyl, 1-naphthylmethoxycarbonyl, 2-(1-naphtyl)ethoxycarbonyl, etc.

The term "$C_{1-12}$alkoxy$C_{1-12}$alkyl" as used herein, alone or in combination, refers to a $C_{1-12}$alkyl as defined herein whereto is attached a $C_{1-12}$alkoxy as defined herein, e.g. methoxymethyl, ethoxymethyl, methoxyethyl, ethoxyethyl, etc.

The term "aryloxy$C_{1-12}$alkyl" as used herein, alone or in combination, refers to a $C_{1-12}$alkyl as defined herein whereto is attached an aryloxy as defined herein, e.g. phenoxymethyl, phenoxydodecyl, 1-naphthyloxyethyl, 2-naphthyloxypropyl, etc.

The term "aralkoxy$C_{1-12}$alkyl" as used herein, alone or in combination, refers to a $C_{1-12}$alkyl as defined herein whereto is attached an aralkoxy as defined herein, e.g. benzyloxymethyl, phenethoxydodecyl, 3-phenylpropoxyethyl, 1-naphthylmethoxypropyl, 2-(1-naphtyl)ethoxymethyl, etc.

The term "thio$C_{1-12}$alkyl" as used herein, alone or in combination, refers to a $C_{1-12}$alkyl as defined herein whereto is attached a group of formula —SR''' wherein R''' is hydrogen, $C_{1-6}$alkyl or aryl, e.g. thiomethyl, methylthiomethyl, phenylthioethyl, etc.

The term "$C_{1-12}$alkoxycarbonylamino" as used herein, alone or in combination, refers to a $C_{1-12}$alkoxycarbonyl as defined herein linked through amino having a free valence bond from the nitrogen atom e.g. methoxycarbonylamino, carbethoxyamino, propoxycarbonylamino, isopropoxycarbonylamino, n-butoxycarbonylamino, tert-butoxycarbonylamino, etc.

The term "aryloxycarbonylamino" as used herein, alone or in combination, refers to an aryloxycarbonyl as defined herein linked through amino having a free valence bond from the nitrogen atom e.g. phenoxycarbonylamino, 1-naphthyloxycarbonylamino or 2-naphthyloxycarbonylamino, etc.

The term "aralkoxycarbonylamino" as used herein, alone or in combination, refers to an aralkoxycarbonyl as defined herein linked through amino having a free valence bond from the nitrogen atom e.g. benzyloxycarbonylamino, phenethoxycarbonylamino, 3-phenylpropoxycarbonylamino, 1-naphthylmethoxycarbonylamino, 2-(1-naphtyl)ethoxycarbonylamino, etc. The term "aryl" is intended to include aromatic rings, such as carboxylic aromatic rings selected from the group consisting of phenyl, naphthyl, (1-naphtyl or 2-naphtyl) optionally substituted with halogen, amino, hydroxy, $C_{1-6}$-alkyl or $C_{1-6}$-alkoxy.

The term "arylene" is intended to include divalent aromatic rings, such as carboxylic aromatic rings selected from the group consisting of phenylene, naphthylene, optionally substituted with halogen, amino, hydroxy, $C_{14}$-alkyl or $C_{1-6}$-alkoxy.

The term "halogen" means fluorine, chlorine, bromine or iodine.

The term "perhalomethyl" means trifluoromethyl, trichloromethyl, tribromomethyl or triiodomethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "acyloxy" as used herein refers to acyl as defined herein linked to an oxygen atom having its free valence bond from the oxygen atom e.g. acetyloxy, propionyloxy, butyryloxy, isobutyryloxy, pivaloyloxy, valeryloxy, and the like.

The term "$C_{1-12}$-alkoxycarbonyl" as used herein refers to a monovalent substituent comprising a $C_{1-12}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "a cyclic ring containing from 5 to 7 carbon atoms" as used herein refers to a monocyclic saturated or unsaturated or aromatic system, wherein the ring may be cyclopentyl, cyclopentenyl, cyclohexyl, phenyl or cycloheptyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen.

The term "aralkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "arycloxy" as used herein refers to phenoxy, 1-naphthyloxy or 2-naphthyloxy.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroaralkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$ alkylsulfinyl" as used herein refers to a monovalent substituent comprising a straight or branched $C_{1-6}$alkyl group linked through a sulfinyl group (—S(=O)—); such as e.g. methylsulfinyl, ethylsulfinyl, isopropylsulfinyl, butylsulfinyl, pentylsulfinyl, and the like.

The term "acylamino" as used herein refers to an amino group wherein one of the hydrogen atoms is substituted with an acyl group, such as e.g. acetamido, propionamido, isopropylcarbonylamino, and the like.

The term "$(C_{3-6}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyly thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$,-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

As used herein, the phrase "heterocyclyl" means a monovalent saturated or unsaturated group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan); 5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan); 5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a 5–6 membered cyclic ring" means an unsaturated or saturated or aromatic system containing one or more carbon atoms and optionally from one to four N, O or S atom(s) or a combination thereof. The phrase "a 5–6 membered cyclic ring" includes, but is not limited to, e.g. cyclopentyl, cyclohexyl, phenyl, cyclohexenyl, pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl, 1,4-dioxolanyl, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines, morpholines); 6-membered heterocycles with three heteroatoms (e.g. 1,3,5-triazine); and 6-membered heterocycles with four heteroatoms.

As used herein, the phrase "5- or 6-membered nitrogen containing ring" refers to a monovalent substituent comprising a monocyclic unsaturated or saturated or aromatic system containing one or more carbon, nitrogen, oxygen or sulfur atoms or a combination thereof and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl and 1,4-dioxolanyl.

Certain of the above defined terms may occur more than once in the above formula (Ia), and upon such occurence each term shall be defined independently of the other.

Pharmaceutically acceptable salts forming part of this invention include salts of the carboxylic acid moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminum salts. Salts may include acid addition salts where appropriate which are, sulphates, nitrates, phosphates, perchlorates, borates, hydrohalides, acetates, tartrates, maleates, citrates, succinates, palmoates, methanesulplionates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The pharmaceutically acceptable salts are prepared by reacting the compound of formula (Ia) with 1 to 4 equivalents of a base such as sodium hydroxide, sodium methoxide, sodium hydride, potassium t-butoxide, calcium hydroxide, magnesium hydroxide and the like, in solvents lilke ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (Ia) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (Ia) may be prepared by hydrolysing the pure diastereomeric amide.

Various polymorphs of compounds of formula (Ia) forming part of this invention may be prepared by crystallization of compounds of formula (Ia) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The invention also relates to a method of preparing the above mentioned compounds.

A compound of formula (Ia) can be prepared as described below:

By carrying out an alkylation reaction between a compound of formula I, wherein A, B, n, p, T, X and Z are as defined previously, and LG is a leaving group preferentially chosen from bromide, iodide, methanesulfonate, or 4-toluenesulfonate,

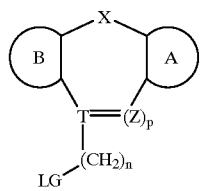

I and a nucleophilic compound of formula II, wherein Ar, m, Q, $R^5$, $R^6$, $R^7$, $R^8$, and Y are as defined previously,

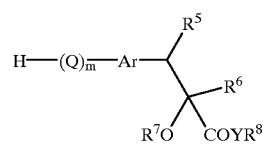

II in the presence of a suitable base such as sodium or potassium carbonate, to give a product of formula II, wherein A, Ar, B, m, n, p, Q, $R^5$, $R^6$, $R^7$, $R^8$, T, X, Y and Z are as defined previously.

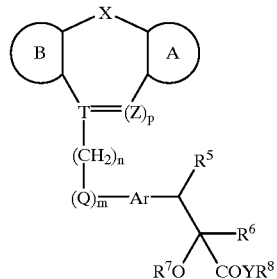

III

Alternatively, by joining a compound of formula I, wherein LG is an alcohol OH group, with a compound of formula II under Mitsunobu conditions, to give a product of formula II, wherein A, Ar, B, m, n, p, Q, $R^5$, $R^6$, $R^7$, $R^8$, T, X, Y and Z are as defined previously.

Alternatively, a compound of formula IV, wherein A, B, p, X and Z are defined previously,

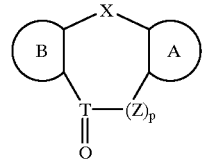

IV may be reacted through a Wittig process with $(Ph_3P)_3P(CH_2)_n$, OH.Br in the presence of a suitable base such as butyllithium, to give compounds of formula V.

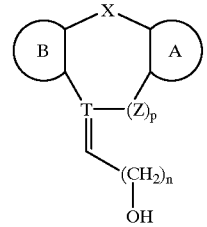

V

Compounds of formula V may then be reacted with compounds of formula II under Mitsunobu conditions to give compounds of formula VI, wherein A, Ar, m, n, p, Q, $R^5$, $R^6$, $R^7R^8$, T, X, Y and Z are as defined previously.

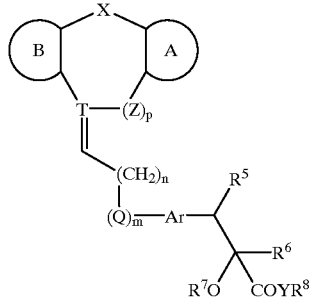

VI

Alternatively, a compound of formula I may be reacted, possibly under transition metal catalysis, with a nucleophilic compound of formula VII,

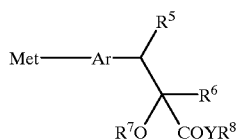

VII wherein "Met" is a metal such as zinc or copper, carrying suitable ligands chosen preferentially from trifluoromethanesulfonate, halide or $C_1$–$C_6$ alkyl, and Ar, $R^5$, $R^6$, $R^7$, $R^8$, and Y are as defined previously, giving rise to products of formula VIII,

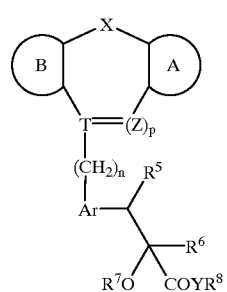

VIII wherein A, B, n, p, $R^5$, $R^6$, $R^7$, $R^8$, T, X, Y and Z are as defined previously.

Alternatively, a nucleophilic compound of formula VII, wherein "Met" is as defined previously, may be reacted with an electrophilic compound of formula IX, wherein A, B, LG, n, p, T, X and Z are as described previously,

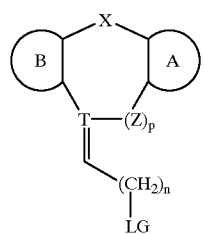

IX giving rise to products of formula X,

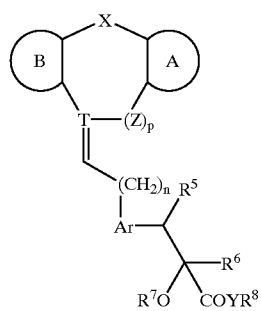

X wherein A, B, n, p, $R^5$, $R^6$, $R^7$, $R^8$, T, X, Y and Z are as defined previously.

Compounds of formula III, VI, VIII and X are all belonging to the compounds of formula (Ia).

PHARMACOLOGICAL METHODS

In Vitro PPAR Alpha and PPAR Gamma Activation Activity

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0.8 μg DNA per well was transfected using FuGene transfection reagent according to the manufacturers instructions (Boehringer-Mannheim). Cells were allowed to express protein for 48 h followed by addition of compound.

Plasmids: Human PPAR α and γ was obtained by PCR amplification using cDNA templates from liver, intestine and adipose tissue respectively. Amplified cDNAs were cloned into pCR2.1 and sequenced. The LBD from each isoform PPAR was generated by PCR (PPARα: aa 167-C-term; PPARγ: aa 165-C-term) and fused to GAL4-DBD by subcloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 μl growth medium including delipidated serum) for 24 h followed by luciferase assay.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter.

PHARMACEUTICAL COMPOSITIONS

In another aspect, the present invention includes within its scope pharmaceutical compositions comprising, as an active ingredient, an effective amount of at least one of the compounds of formula (Ia) or a pharmaceutically acceptable salt thereof together with a pharmaceutically acceptable carrier or diluent.

Pharmaceutical compositions containing a compound of the present invention may be prepared by conventional techniques, e.g. as described in *Remington: The Science and Practice of Pharmacy*, 19$^{th}$ Ed., 1995. The compositions may appear in conventional forms, for example capsules, tablets, aerosols, solutions, suspensions or topical applications.

Typical compositions include a compound of formula (Ia) or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound to the appropriate or desired site of action, such as oral, nasal, pulmonary, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula (Ia) dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 5 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula (Ia) admixed with a pharmaceutically acceptable carrier or diluent.

In a further aspect, the present invention relates to a method of treating and/or preventing type I or type II diabetes.

In a still further aspect, the present invention relates to the use of one or more compounds of formula (Ia) or pharmaceutically acceptable salts thereof for the preparation of a medicament for the treatment and/or prevention of type I or type II diabetes.

Any novel feature or combination of features described herein is considered essential to this invention.

What is claimed is:

1. A compound of formula (Ia)

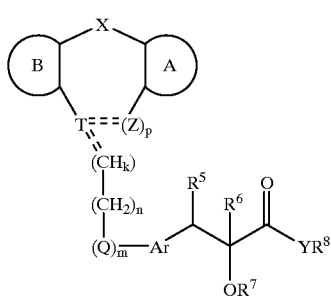

(Ia)

wherein ring A represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkylamino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

ring B represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

X is a valence bond, —(CHR$^9$)—, —(CHR$^9$)—CH$_2$—, —CH=CH—, —(CHR$^9$)—CH=CH—, —(CHR$^9$)—CH$_2$—CH$_2$—, —CH=(CR$^9$)—, wherein R$^9$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, $C_{1-6}$alkoxy, amino optionally substituted with one or more $C_{1-6}$alkyl, perhalomethyl or aryl;

T is >CH— or >C<;

Z is —CH$_2$— or =CH—;

Q is —O—, —S—, >SO$_2$, >NR$^{16}$, wherein R$^{16}$ is hydrogen or $C_{1-6}$alkyl;

k is 1 or 2;

T===(Z)$_p$ and T===(CH$_k$) independently of each other represents a single bond or a double bond, provided that both are not a double bond at the same time;

Ar represents arylene, heteroarylene, or a divalent heterocyclic group optionally substituted with one or more $C_{1-6}$alkyl or aryl;

R$^5$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl or aralkyl; optionally substituted with one or more halogen, perhalomethyl, hydroxy, nitro or cyano; or R$^5$ forms a bond together with R$^6$;

R$^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl, acyl or aralkyl; optionally substituted with one or more halogen, perhalomethyl, hydroxy, nitro or cyano; or R$^6$ forms a bond together with R$^5$;

R$^7$ represents hydrogen, $C_{1-12}$alkyl, $C_{4-12}$-alkenynyl, $C_{2-12}$-alkenyl, $C_{2-12}$-alkynyl, aryl, aralkyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, acyl, heterocyclyl, heteroaryl or heteroaralkyl groups; optionally substituted with one or more halogen, perhalomethyl, hydroxy, nitro or cyano;

R$^8$ represents hydrogen, $C_{1-12}$alkyl, $C_{4-12}$-alkenynyl, $C_{2-12}$-alkenyl, $C_{2-12}$-alkynyl, aryl, aralkyl, heterocyclyl, heteroaryl or heteroaralkyl groups; optionally substituted with one or more halogen, perhalomethyl, hydroxy, nitro or cyano;

Y represents oxygen, sulphur or NR$^{10}$, where R$^{10}$ represents hydrogen, $C_{1-12}$alkyl, aryl, hydroxy$C_{1-12}$alkyl or aralkyl groups or when Y is NR$^{10}$, R$^8$ and R$^{10}$ may form a 5 or 6 membered nitrogen containing ring, optionally substituted with one or more $C_{1-6}$alkyl;

p is an integer ranging from 0 to 1, n is an integer ranging from 0 to 3 and m is an integer ranging from 0 to 1;

provided that A or B does not represent phenyl;

or a pharmaceutically acceptable salt thereof.

2. The compound of claim 1 wherein ring A represents a 5–6 membered cyclic ring, optionally substituted with one or more halogen, perhalomethyl, hydroxy, cyano, or $C_{1-7}$alkyl, $C_{4-7}$alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano.

3. The compound of claim 1 wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, or aralkoxycarbonylaamino.

4. The compound of claim 1 wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, acylamino, $C_{1-7}$alkylamino, arylamino, aralkylamino, $C_{1-7}$alkoxy$C_{1-7}$alkyl, aryloxy$C_{1-7}$alkyl, aralkoxy$C_{1-7}$alkyl, or $C_{1-7}$alkylthio.

5. The compound of claim 1 wherein ring A represents a 5–6 membered cyclic ring, optionally substituted with one or more halogen, $C_{1-7}$alkyl, $C_{1-7}$alkoxy, aryl, or aryloxy.

6. The compound of claim 1 wherein ring A represents a 5–6 membered cyclic ring, optionally substituted with one or more $C_{1-7}$alkoxy.

7. The compound of claim 1 wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano.

8. The compound of claim 1 wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkylamino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylainino, aryloxycarbonylamino, or aralkoxycarbonylamino.

9. The compound of claim 1 wherein ring B represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, acylamino, $C_{1-7}$alkylamino, arylamino, aralkylamino, $C_{1-7}$alkoxy$C_{1-7}$alkyl, aryloxy$C_{1-7}$alkyl, aralkoxy$C_{1-7}$alkyl,or $C_{1-7}$alkylthio.

10. The compound of claim 1 wherein ring B represents a 5–6 membered cyclic ring, optionally substituted with one or more halogen, $C_{1-7}$alkyl, $C_{1-7}$alkoxy, aryl, or aryloxy.

11. The compound of claim 1 wherein ring B represents a 5–6 membered cyclic ring, optionally substituted with one or more $C_{1-7}$alkoxy.

12. The compound of claim 1 wherein X is a valence bond, —$(CHR^9)$—, —$(CHR^9)$—$CH_2$—, —$CH=CH$—, —$(CHR^9)$—$CH=CH$—, —$(CHR^6)$—$CH_2$—$CH_2$—, —$CH=(CR^9)$—, wherein $R^9$ is hydrogen, halogen, hydroxy, cyano, $C_{1-7}$alkyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-7}$alkyl-amino, arylamino, aralkylamino, amino$C_{1-7}$alkyl, $C_{1-7}$alkoxycarbonyl, aryloxycarbonyl, aralkoxycarbonyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, halogen, $C_{1-6}$alkoxy, amino optionally substituted with one or more $C_{1-6}$alkyl, perhalomethyl or aryl.

13. The compound of claim 1 wherein X is a valence bond, —$(CHR^9)$—, —$(CHR^9)$—$CH_2$—, —$CH=CH$—, —$(CHR^9)$—$CH=CH$—, —$(CHR^6)$—$CH_2$—$CH_2$—, —$CH=(CR^9)$—, wherein $R^9$ is hydrogen, halogen, hydroxy, $C_{1-7}$alkyl, $C_{1-7}$alkoxy, or aryl.

14. The compound of claim 1 wherein X is a valence bond, —$(CHR^9)$—, —$(CHR^9)$—$CH_2$—, —$CH=CH$—, —$CH=(CR^9)$—, wherein $R^9$ is hydrogen, halogen, hydroxy, $C_{1-7}$alkyl, $C_{1-7}$alkoxy, or aryl.

15. The compound of claim 1 wherein Q is —O—, —S—, >$SO_2$, >$NR^{16}$, wherein $R^{16}$ is hydrogen or methyl.

16. The compound of claim 1 wherein Ar is arylene optionally substituted with one or more $C_{1-6}$alkyl or aryl.

17. The compound of claim 1 wherein Ar is phenyl.

18. The compound of claim 1 wherein $R^5$ is hydrogen, hydroxy, halogen, $C_{1-7}$alkoxy, $C_{1-7}$alkyl, $C_{4-7}$-alkenynyl, $C_{2-7}$-alkenyl, $C_{2-7}$-alkynyl or aralkyl; or $R^5$ forms a bond together with $R^6$.

19. The compound of claim 1 wherein $R^5$ is hydrogen, or $R^5$ forms a bond together with $R^6$.

20. The compound of claim 1 wherein $R^6$ is hydrogen, $C_{1-7}$alkoxy, $C_{1-7}$alkyl, $C_{4-7}$-alkenynyl, $C_{2-7}$-alkenyl, $C_{2-7}$-alkynyl, acyl or aralkyl; or $R^6$ forms a bond together with $R^5$.

21. The compound of claim 1 wherein $R^6$ is hydrogen or $R^6$ forms a bond together with $R^5$.

22. The compound of claim 1 wherein $R^7$ is hydrogen, $C_{1-7}$alkyl, $C_{4-7}$-alkenynyl, $C_{2-7}$-alkenyl, $C_{2-7}$-alkynyl, aryl, aralkyl, $C_{1-7}$alkoxy$C_{1-7}$alkyl, $C_{1-7}$alkoxycarbonyl, aryloxycarbonyl, $C_{1-7}$alkylaminocarbonyl, arylaminocarbonyl, acyl, heterocyclyl, heteroaryl or heteroaralkyl.

23. The compound of claim 1 wherein $R^7$ is hydrogen, $C_{1-7}$alkyl, $C_{4-7}$-alkenynyl, $C_{2-7}$-alkenyl, or $C_{2-7}$-alkynyl.

24. The compound of claim 1 wherein $R^7$ is $C_{1-2}$alkyl.

25. The compound of claim 1 wherein $R^8$ is hydrogen, $C_{1-7}$alkyl, $C_{4-7}$-alkenynyl, $C_{2-7}$-alkenyl, $C_{2-7}$-alkynyl, aryl, aralkyl, heterocyclyl, heteroaryl or heteroaralkyl groups; optionally substituted with one or more halogen, perhalomethyl, hydroxy, nitro or cyano.

26. The compound of claim 1 wherein $R^8$ is hydrogen, $C_{1-7}$alkyl, $C_{4-7}$-alkenynyl, $C_{2-7}$-alkenyl, $C_{2-7}$-alkynyl, aryl or aralkyl.

27. The compound of claim 1 wherein $R^8$ is hydrogen or $C_{1-2}$alkyl.

28. The compound of claim 1 wherein Y is oxygen, sulphur or $NR^{10}$, wherein $R^{10}$ is hydrogen, $C_{1-7}$alkyl, aryl, hydroxy$C_{1-7}$alkyl or aralkyl.

29. The compound of claim 1 wherein Y is oxygen.

30. The compound of claim 1 wherein A is a 5 membered cyclic ring containing S.

31. The compound of claim 1 wherein B is a 5 membered cyclic ring containing S.

32. The compound of claim 1 wherein X is —(CHR$^9$)—CH$_2$—, wherein R$^9$ is H.

33. The compound of claim 1 wherein T is >C<.

34. The compound of claim 1 wherein p is 0.

35. The compound of claim 1 wherein k is 1.

36. The compound of claim 1 wherein n is 1.

37. The compound of claim 1 wherein m is 1.

38. The compound of claim 1 wherein Q is —O—.

39. The compound of claim 1 wherein Ar is phenylene.

40. The compound of claim 1 wherein R$^5$ is H.

41. The compound of claim 1 wherein R$^6$ is H.

42. The compound of claim 1 wherein R$^7$ is ethyl.

43. The compound of claim 1 wherein R$^8$ is H.

44. The compound of claim 1 which is

3-{4-[2-(4,5-dihydro-cyclohepta[2,1-b4,5-b']dithiophen-9-ylidene)-ethoxy]-phenyl}-2etoxypropionic acid, Ethyl 3-{4-[2-(9H-1,8-diazafluoren-9-yl)-ethoxy]-phenyl}-2-ethoxypropionate, 3-{4-[2-(9H-1,8-Diazafluoren-9-yl)-ethoxy]-phenyl}-2-ethoxypropionic acid, Ethyl 3-{4-[3-(9H-1,8-Diazafluoren-9-yl)-propoxy]-phenyl}-2-ethoxypropionate, 3-{4-[3-(9H-1,8-Diazafluoren-9-yl)-propoxy]-phenyl}-2-ethoxypropionic acid, Ethyl 3-{4-[2-(9H1,8-Diazafluoren-9-yl)-ethoxy]-phenyl}-2-methoxypropionate, 3-{4-[2-(9H-1,8-Diazafluoren-9-yl)-ethoxy]-phenyl}-2-methoxypropionic acid, Ethyl 3-{4-[3-(9H-1,8-Diazafluoren-9-yl)-propoxy]-phenyl}-2-methoxypropionate, 3-{4-[3-(9H-1,8-Diazafluoren-9-yl)-propoxy]-phenyl}-2-methoxypropionic acid, Ethyl 3-{4-[2-(1,8-diazafluoren-9-ylidene)-ethoxy]-phenyl}-2-ethoxypropionate, 3-{4-[2-(1,8-Diazafluoren-9-ylidene)-ethoxy]-phenyl}-2-ethoxypropionic acid, Ethyl 3-{4-[3-(1,8-Diazafluoren-9-ylidene)-propoxy]-phenyl}-2-ethoxypropionate, 3-{4-[3-(1,8-Diazafluoren-9-ylidene)-propoxy]-phenyl}-2-ethoxypropionic acid, Ethyl 3-{4-[2-(1,8-Diazafluoren-9-ylidene)-ethoxy]-phenyl}-2-methoxypropionate, 3-{4-[2-(1,8-Diazafluoren-9-ylidene)-ethoxy]-phenyl}-2-methoxypropionic acid, Ethyl 3-{4-[3-(1,8-Diazafluoren-9-ylidene)-propoxyl-phenyl}-2-methoxypropionate, 3-{4-[3-(1,8-Diazafluoren-9-ylidene)-propoxy]-phenyl}-2-methoxypropionic acid, Ethyl 3-{4-[2-(9H-1,7-diazafluoren-9-yl)-ethoxy]-phenyl}-2-ethoxypropionate, 3-{4-[2-(9H-1,7-Diazafluoren-9-yl)-ethoxy]-phenyl}-2-ethoxypropionic acid, Ethyl 3-{4-[3-(9H-1,7-Diazafluoren-9-yl)-propoxy]-phenyl}-2-ethoxypropionate, 3-{4-[3-(9H-1,7-Diazafluoren-9-yl)-propoxy]-phenyl}-2-ethoxypropionic acid, Ethyl 3-{4-[2-(9H-1,7-Diazafluoren-9-yl)-ethoxy]-phenyl}-2-methoxypropionate, 3-{4-[2-(9H-1,7-Diazafluoren-9-yl)-ethoxyl-phenyl}2-methoxypropionic acid, Ethyl 3-{4-[3-(9H-1,7-Diazafluoren-9-yl)-propoxy]-phenyl}-2-methoxypropionate, 3-{4-[3-(9H-1,7-Diazafluoren-9-yl)-propoxy]-phenyl}-2-methoxypropionic acid, Ethyl 3-{4-[2-(1,7-diazafluoren-9-ylidene)-ethoxy]-phenyl}-2-ethoxypropionate, 3-{4-[2-(1,7-Diazafluoren-9-ylidene)-ethoxy]-phenyl}-2-ethoxypropionic acid, Ethyl 3-{4-[3-(1,7-Diazafluoren-9-ylidene)-propoxy]-phenyl}]2-ethoxypropionate, 3-{4-[3-(1,7-Diazafluoren-9-ylidene)-propoxy]-phenyl}-2-ethoxypropionic acid, Ethyl 3-{4-[2-(1,7-Diazafluoren-9-ylidene)-ethoxy]-phenyl}-2-methoxypropionate, 3-{4-[2-(1,7-Diazafluoren-9-ylidene)-ethoxy]-phenyl}-2-methoxypropionic acid, Ethyl 3-{4-[3-(1,7-Diazafluoren-9-ylidene)-propoxy]-phenyl}-2-methoxypropionate, 3-{4-[3-(1,7-Diazafluoren-9-ylidene)-propoxy]-phenyl}-2-methoxypropionic acid, Ethyl 3-{4-[2-(9H-2,7-diazafluoren-9-yl)-ethoxy]-phenyl}-2-ethoxypropionate, 3-{4-[2-(9H-2,7-Diazafluoren-9-yl)-ethoxy]-phenyl}-2-ethoxypropionic acid, Ethyl 3-{4-[3-(9H-2,7-Diazafluoren-9-yl)-propoxy]-phenyl}-2-ethoxypropionate, 3-{4-[3-(9H-2,7-Diazafluoren-9-yl)-propoxy]-phenyl}-2-ethoxypropionic acid, Ethyl 3-{4-[2-(9H-2,7-Diazafluoren-9-yl)-ethoxy]-phenyl}-2-methoxypropionate, 3-{4-[2-(9H-2,7-Diazafluoren-9-yl)-ethoxy]-phenyl}-2-methoxypropionic acid, Ethyl 3-{4-[3-(9H-2,7-Diazafluoren-9-yl)-propoxy]-phenyl}-2-methoxypropionate, 3-{4-[3-(9H-2,7-Diazafluoren-9-yl)-propoxy]-phenyl}-2-methoxypropionic acid, Ethyl 3-{4-[2-(2,7-diazafluoren-9ylidene)-ethoxy]-phenyl}-2-ethoxypropionate, 3-{4-[2-(2,7-Diazafluoren-9-ylidene)-ethoxy]-phenyl}-2-ethoxypropionic acid, Ethyl 3-{4-[2-(2,7-diazafluoren-9-ylidene)-ethoxy]-phenyl}-2-ethoxypropionate, 3-{4-[2-(2,7-Diazafluoren-9-ylidene)-ethoxy]-phenyl}-2-ethoxypropionic acid, Ethyl 3-{-[3-(2,7-Diazafluoren-9-ylidene)-propoxy]-phenyl}-2-methoxypropionate, 3-{4-[3-(2,7-Diazafluoren-9-ylidene)-propoxy]-phenyl}-2-methoxypropionic acid, Ethyl 3-{4-[3-(2,7-Diazafluoren-9-ylidene)-propoxy]-phenyl}-2-methoxypropionate, 3-{4-[2-(2,7-Diazafluoren-9-ylidene)-propoxy]-phenyl}-2-methoxypropionic acid, Ethyl 3-{4-[2-(9H-3,6-diazafluoren-9-yl)-ethoxy]-phenyl}-2-ethoxypropionate, 3-{4-[3-(9H-3,6-Diazafluoren-9-yl)-propoxy]-phenyl}-2-ethoxypropionic acid, Ethyl 3-{4-[3-(9H-3,6-diazafluoren-9-yl)-propoxy]-phenyl}-2-ethoxypropionate, 3-{4-[3-(9H-3,6-Diazafluoren-9-yl)-propoxy]-phenyl}-2-ethoxypropionic acid, Ethyl 3-{4-[3-(9H-3,6-diazafluoren-9-yl)-propoxy]-phenyl}-2-methoxypropionate,
3-{4-[2-(9H-3,6-Diazafluoren-9-yl)-ethoxy)-phenyl}-2-methoxypropionic acid,
Ethyl 3-{4-[3-(9H-3,6-diazafluoren-9-yl)-propoxy]-phenyl}-2-methoxypropionate,
3-{4-[3-(9H-3,6-Diazafluoren-9-yl)-propoxy]-phenyl}-2-methoxypropionic acid,
Ethyl 3-{4-[2-(3,6-diazafluoren-9-ylidene)-ethoxy]-phenyl}-2-ethoxypropionate,
3-{4-[2-(3,6-Diazafluoren-9-ylidene)-ethoxyl-phenyl}-2-ethoxypropionic acid,
Ethyl 3-{4-[3-(3,6-diazafluoren-9-ylidene)-propoxy]-phenyl}-2-ethoxypropionate,
3-{4-[3-(3,6-Diazafluoren-9-ylidene)-propoxy]-phenyl}-2-ethoxypropionic acid,
Ethyl 3-{4-[2-(3,6-diazafluoren-9-ylidene)-ethoxy]-phenyl}-2-methoxypropionate,
3-{4-[2-(3,6-Diazafluoren-9-ylidene)-ethoxy]-phenyl}-2-methoxypropionic acid,
Ethyl 3-{4-[3-(3,6-Diazafluoren-9-ylidene)-propoxy]-phenyl}-2-methoxypropionate,
3-{4-[3-(3,6-Diazafluoren-9-ylidene)-propoxy]-phenyl}-2-methoxypropionic acid,
Ethyl 3-{4-[2-(cyclopenta[1,2-b;4,3-b']difuran-7-ylidene)-ethoxy]-phenyl}-2-ethoxypropionate,
3-{4-2-(Cyclopenta[1,2-b;4,3-b']difuran-7-ylidene)-ethoxy]-phenyl}-2-ethoxypropionic acid,
Ethyl 3-{4-[3-(cyclopenta[1,2-b;4,3-b']difuran-7-ylidene)-propoxy]-phenyl}-2-ethoxypropionate,
3-{4-3-(Cyclopenta1,2-b;4,3-b']difuran-7-ylidene)-propoxy]-phenyl}-2-ethoxypropionic acid,
Ethyl 3-{4-[2-(cyclopenta[1,2-b;4,3-b']difuran-7-ylidene)-ethoxy]-phenyl}-2-methoxy-propionate,
3-{4-[2-(Cyclopenta[1,2-b;4,3-b']difuran-7-ylidene)-ethoxy]-phenyl}-2-methoxypropionic acid,
Ethyl 3-{4-[3-(cyclopenta[1,2-b;4,3-b']difuran-7-ylidene)-propoxy]-phenyl}-2-methoxypropionate,
3-{4-[3-(Cyclopenta[1,2-b;4,3-b']difuran-7-ylidene)-propoxy]-phenyl}-2-methoxy-propionic acid,
Ethyl 3-{4-[2-(7H-cyclopenta[1,2-b;4,3-b']difuran-7-yl)-ethoxy]-phenyl}-2-ethoxypropionate,
3-{4-[2-(7H-Cyclopenta[1,2-b;4,3-b']difuran-7-yl)-ethoxy]-phenyl}-2-ethoxypropionic acid,
Ethyl 3-{4-[3-(7H-cyclopenta[1,2-b;4,3-b']difuran-yl)-propoxy]-phenyl}-2-ethoxy-propionate
3-{4-[3-(7H-Cyclopenta[1,2-b;4,3-b']difuran-7-yl)-ethoxy]-phenyl}-2-ethoxypropionic acid,
Ethyl 3-{4-[2-(7H-cyclopenta[1,2-b;4,3-b']difuran-7-yl)-ethoxy]-phenyl}-2-methoxy-propionate,
3-{4-[2-(7H-Cyclopenta[1,2-b;4,3-b']difuran-7-yl)-ethoxy]-phenyl}-2-methoxypropionic acid,
Ethyl 3-{4-[3-(7H-cyclopenta[1,2-b;4,3-b']difuran-7-yl)-propoxy]-phenyl}-2-methoxypropionate,
3-{4-[3-(7H-Cyclopenta[1,2-b;4,3-b']difuran-7-yl)-propoxy]-phenyl}-2-methoxy-propionic acid,
Ethyl 3-{4-[2-(cyclopenta[1,2-b;4,3-b']dithiophen-7-ylidene)-ethoxy]-phenyl}-2-ethoxypropionate,
3-{4-[2-(Cyclopenta[1,2-b;4,3-b']dithiophen-7-ylidene)-ethoxy]-phenyl}-2-ethoxypropionic acid,
Ethyl 3-{4-[3-(cyclopenta[1,2-b;4,3-b']dithiophen-7-ylidene)-propoxy]-phenyl}-2-ethoxypropionate,
3-{4-[3-(Cyclopenta[1,2-b;4,3-b']dithiophen-7-ylidene)-propoxy]-phenyl}-2-ethoxypropionic acid,
Ethyl 3-{4-[2-(cyclopenta[1,2-b;4,3-b']dithiophen-7-ylidene)-ethoxy]-phenyl}-2-methoxypropionate,
3-{4-[2-(Cyclopenta[1,2-b;4,3-b']dithiophen-7-ylidene)-ethoxy]-phenyl}-2-methoxypropionic acid,
Ethyl 3-{4-[3-(cyclopenta[1,2-b;4,3-b']dithiophen-7-ylidene)-propoxy]-phenyl}-2-methoxypropionate,
3-{4-[3-(Cyclopenta[1,2-b;4,3-b']dithiophen-7-ylidene)-propoxy]-phenyl}-2-methoxy-propionic acid,
Ethyl 3-{4-[2-(7H-cyclopenta[1,2-b;4,3-b']dithiophen-7-yl)-ethoxy]-phenyl}-2-ethoxypropionate,
3-{4-[2-(7H-Cyclopenta[1,2-b;4,3-b']dithiophen-7-yl)-ethoxy]-phenyl}-2-ethoxypropionic acid,
Ethyl 3-{4-[3-(7H-cyclopenta[1,2-b;4,3-b']dithiophen-7-yl)-propoxy]-phenyl}-2-ethoxypropionate,
3-{4-[3-(7H-Cyclopenta[1,2-b;4,3-b']dithiophen-7-yl)-propoxy]-phenyl}-2-ethoxypropionic acid,
Ethyl 3-{4-[2-(7H-cyclopenta[1,2-b;4,3-b']dithiophen-7-yl)-ethoxy]-phenyl}-2-methoxypropionate,
3-{4-[2-(7H-Cyclopenta[1,2-b;4,3-b']dithiophen-7-yl)-ethoxy]-phenyl}-2-methoxypropionic acid,
Ethyl 3-{4-[3-(7H-cyclopenta[1,2-b;4,3-b']dithiophen-7y)-propoxy]-phenyl}-2-methoxypropionate, or
3-{4-[3-(7H-Cyclopenta[1,2-b;4,3-b']dithiophen-7-yl)-propoxy]-phenyl}-2-methoxy-propionic acid;

or a pharmaceutically acceptable salt thereof.

45. The compound of claim 1 which is
3-{4-[2-(4,5-dihydro-cyclohepta[2,1-b4,5-b']dithiophen-9-ylidene)-ethoxy]-phenyl}-2-ethoxypropionic acid;

or a pharmaceutically acceptable salt thereof.

46. A pharmaceutical composition comprising, as an active ingredient, an effective amount of the compound of claim 1 together with a pharmaceutically acceptable carrier or diluent.

47. The composition of claim 46 in unit dosage form, comprising from about 0.05 to about 100 mg of the compound.

48. The pharmaceutical composition of claim 46 wherein the route of administration is oral, nasal, transdermal, pulmonal, or parenteral.

49. A method of treating or preventing conditions mediated by nuclear receptors, the method comprising administering to a subject in need thereof an effective amount of the compound of claim 1.

50. The method of claim 49, wherein the nuclear receptors are the Peroxisome Proliferator-Activated Receptors (PPAR).

51. A method of treating or preventing diabetes or obesity, the method comprising administering to a subject in need thereof an effective amount of the compound of claim 1.

52. The method of claim 49, wherein the effective amount of the compound is in the range of from about 0.05 to about 100 mg per day.

* * * * *